(12) United States Patent
Heggs et al.

(10) Patent No.: US 8,128,874 B2
(45) Date of Patent: Mar. 6, 2012

(54) PRESSURIZED DETECTORS SUBSTANCE ANALYZER

(75) Inventors: Eric T. Heggs, Camden, OH (US); Edward K. Price, Liberty Township, OH (US); Stephen R. Proffitt, Cincinnati, OH (US)

(73) Assignee: Teledyne Instruments, Inc., Thousand Oaks, CA (US)

( * ) Notice: Subject to any disclaimer, the term of this patent is extended or adjusted under 35 U.S.C. 154(b) by 114 days.

(21) Appl. No.: 12/692,115

(22) Filed: Jan. 22, 2010

(65) Prior Publication Data
US 2010/0116027 A1   May 13, 2010

Related U.S. Application Data

(62) Division of application No. 11/708,926, filed on Feb. 21, 2007, now abandoned.

(51) Int. Cl.
*G01N 7/00* (2006.01)

(52) U.S. Cl. ......... 422/83; 356/437; 73/31.04; 436/181; 250/339

(58) Field of Classification Search ............. 422/80, 422/83; 436/101, 178, 146; 356/437; 73/31.04; 250/339
See application file for complete search history.

(56) References Cited

U.S. PATENT DOCUMENTS

| | | | | |
|---|---|---|---|---|
| 4,271,124 A | * | 6/1981 | Speeter | 422/82.09 |
| 5,429,805 A | * | 7/1995 | Uno et al. | 422/83 |
| 6,375,900 B1 | * | 4/2002 | Lee-Alvarez et al. | 422/80 |
| 6,444,474 B1 | * | 9/2002 | Thomas et al. | 436/146 |

* cited by examiner

*Primary Examiner* — Sally Sakelaris
(74) *Attorney, Agent, or Firm* — K&L Gates LLP

(57) ABSTRACT

A method to measure the concentration of a constituent element in a gas sample contained in an analyzer. A sample cell of a detector has an inlet and an outlet. The outlet of the sample cell is sealed. A predetermined mass of a gas sample is received through the inlet into the sample cell over a predetermined pressurization period until substantially the entire mass of the gas sample contained in the analyzer is contained within the sample cell. The gas sample is pressurized to a predetermined pressure over the pressurization period. A concentration of a constituent element in the pressurized gas sample is determined.

20 Claims, 10 Drawing Sheets

US 8,128,874 B2

PRESSURIZED DETECTORS SUBSTANCE ANALYZER

CROSS REFERENCE TO RELATED APPLICATION

This application is a divisional of U.S. patent application Ser. No. 11/708,926 filed Feb. 21, 2007, entitled PRESSURIZED DETECTORS SUBSTANCE ANALYZER, now abandoned, the entire disclosure of which is hereby incorporated by reference herein.

FIELD

Sample analyzers comprising pressurized detectors employed in analytical instruments for substance analysis.

BACKGROUND

Chemical sample analyzers may be employed to measure the content of a particular element or compound (constituent) in a sample (e.g., specimen). Throughout this description, it will be understood by those skilled in the art that the term constituent element may be used to refer to an analyte, element, compound, component and/or any substance in the sample. Some chemical sample analyzers may be adapted to measure the content of carbon, sulfur, nitrogen, among others, of a sample. Carbon analyzers may be employed to measure the total organic carbon (TOC), the inorganic carbon (IC), the total carbon (TC; TC=TOC+IC), purgeable organic carbon (POC) and/or non-purgeable organic carbon (NPOC) content of the sample. TOC measurement processes may include oxidizing organic carbon in the sample, detecting and quantifying the oxidized carbon (e.g., $CO_2$) and presenting the result in units of mass of carbon per volume of the sample.

Carbon analyzers are used in a variety of industries to measure, monitor and analyze analytical information relating to the carbon content of a given sample. Measuring the carbon content in liquids such as drinking water, treated or untreated wastewater and ultra pure water for pharmaceutical or clean room applications is a routine way to assess the purity of the liquid sample. Monitoring the carbon content of wastewater is particularly significant in the chemical, pharmaceutical, semiconductor, food and beverage industries. Other areas that require careful monitoring of carbon content include the paint, resin and coating industries. Carbon analysis also can be essential for ascertaining whether drinking water, groundwater, soils and wastewater comply with government regulations. Carbon analysis also may be performed to protect process equipment such as boilers, turbines and purification devices because organic materials such as carbon may contaminate the process equipment.

Furthermore, there is an increasing interest in measuring, monitoring and analyzing carbon levels in solids or semi-solid specimens such as soils, clays and sediments. Accordingly, these solids or semi-solids can be measured, monitored and analyzed for carbon content using known analyzer accessories.

Nitrogen analyzers may be employed to measure the nitrogen content in the sample. Nitrogen in a sample may be converted to nitric oxide (NO). The NO is mixed with ozone to form $NO_2^*$ ($NO_2$ in excited state). When the $NO_2^*$ returns to its ground state it gives off energy in the form of light. This process is known as chemiluminescence. The amount of light given off is proportional to the amount of NO in the sample.

Conventional sample analyzers employ a flow-through type detector technique to measure the content of a particular constituent in a sample. Flow-through technology provides a certain level of sensitivity in the measured content. There is a need for a sample analyzer to measure the content of a constituent in a gas sample with increased sensitivity over the conventional flow-through type detector techniques.

SUMMARY

A beam of radiation having a specific wavelength is directed through a pressurized gas sample in a cell. The specific wavelength is absorbed by a constituent of the sample if present. The amount radiation at the specific wavelength that is absorbed directly correlates to the amount of the constituent present in the cell.

In various embodiments, a method is provided to measure the concentration of a constituent element in a sample. In one embodiment, the method is to measure the concentration of a constituent element in a gas sample contained in an analyzer and includes sealing an outlet of a sample cell of a detector. A predetermined mass of a gas sample is received through an inlet into the sample cell over a predetermined pressurization period until substantially the entire mass of the gas sample contained in the analyzer is contained within the sample cell. The gas sample is pressurized to a predetermined pressure over the pressurization period. A concentration of a constituent element in the pressurized gas sample is determined.

DESCRIPTION

Figure 1:
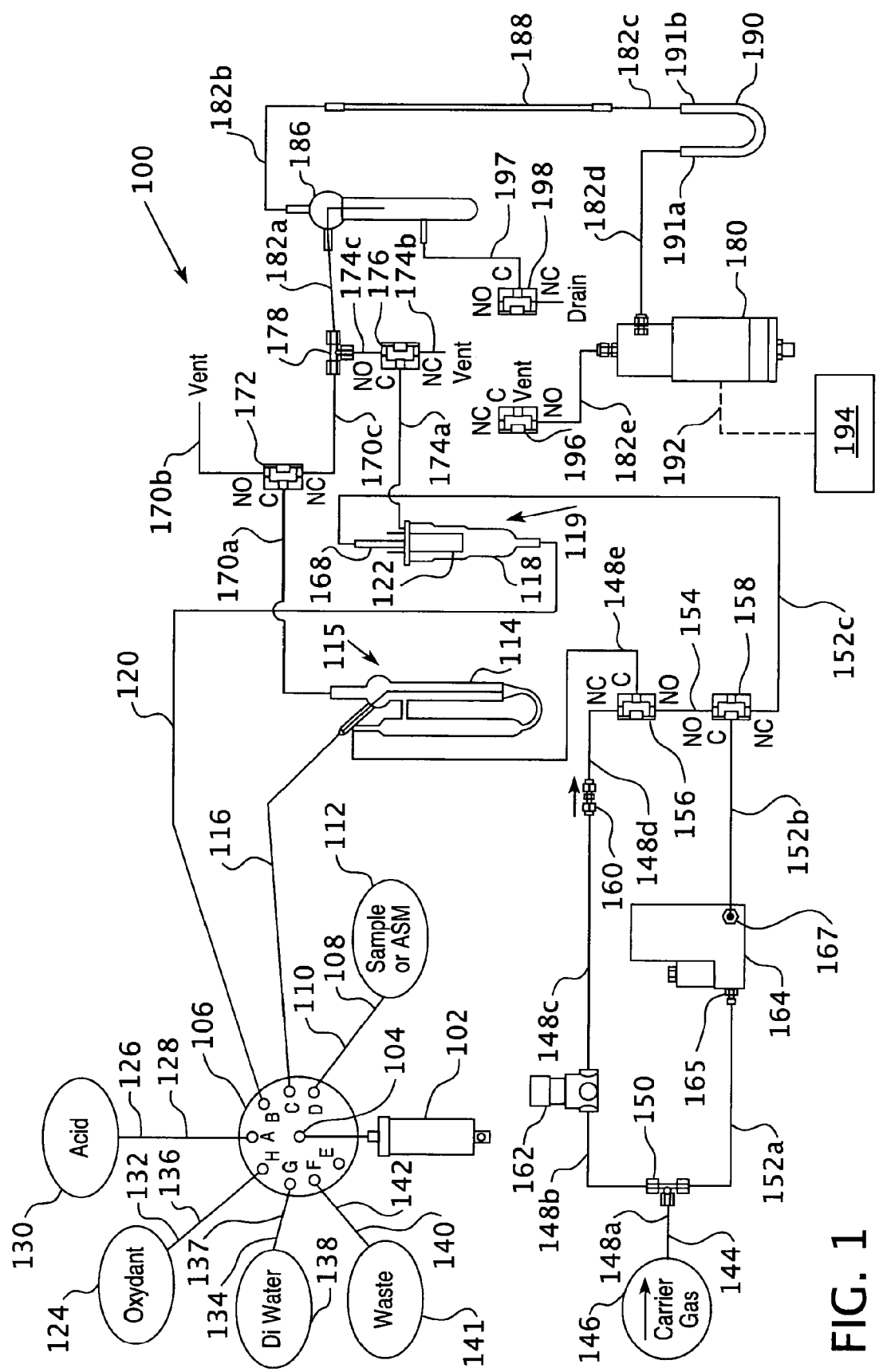
FIG. 1 illustrates a flow diagram of one embodiment of an analyzer.

Various embodiments are disclosed of analytical instruments comprising a sample analyzer and pressurized detector employed to monitor, measure and/or analyze an analytical sample for a predetermined substance referred to as a constituent element. The sample analyzer may be employed to monitor, measure and/or analyze constituent elements in an analytical sample. The content of the constituent element may be unknown. In various embodiments the constituent element to be analyzed, monitored or detected may be predetermined. In one embodiment the constituent element may be carbon, for example. In addition, also disclosed is one embodiment of a method for pressurizing a detector in an analytical instrument as the instrument monitors, measures and/or analyzes the sample for a constituent element. The embodiments, however, are not limited in this context and the embodiments may be readily adapted for monitoring, measuring and/or analyzing any sample for any predetermined constituent element, component, substance and/or compound in an analytical sample.

In one embodiment, a pressurized sample analyzer may be employed to measure the $CO_2$ produced by the oxidation of carbon in a sample. The pressurized sample analyzer may comprise a pressurized detector adapted to measure the $CO_2$ content of a sample. In various embodiments, the pressurized sample analyzer may be adapted to analyze and measure the contents of a variety of unknown substances or constituent elements in an analytical sample including Organic Carbon (OC), IC, POC, NPOC and/or TC. The pressurized sample analyzer may employ a pressurized detection technique or a static read technique to oxidize and sweep a predetermined (e.g., specific) carbon component (e.g., $CO_2$ gas compound) with an inert carrier gas such as nitrogen gas, for example, to a sealed detector where the carbon component is analyzed. Once a suitable, substantial or entire quantity of the carbon component has been swept from the sample into a cell of the detector, the carbon component is pressurized and single or multiple measurements (e.g., readings) are made to determine the amount of the carbon component contained in the pressurized cell. The single or multiple measurements may be referred to as "static measurements" because a quantity of the sample is trapped under pressure in the cell during the measurement. These static measurements correlate directly to the concentration of the specific carbon constituent element contribution in the sample. In this particular technique, the same carbon component is contained in the pressurized detector cell simultaneously during the measurement process. This technique provides increased sensitivity in the measurement. To make this type of static measurement the detector may be pressurized to a suitable pressure above atmospheric (e.g., ambient) pressure. The detector may be pressurized from one atmosphere up to or beyond several atmospheres (e.g., two or more atmospheres).

Generally two types of carbon constituent elements may be present in a given sample, OC such as complex hydrocarbons and IC such as carbonate, bicarbonate and dissolved $CO_2$. The TC content of a sample includes the TOC content plus the total IC content. Represented formulaically:

$$TC=TOC+IC$$

Thus, if the TOC is the quantity of interest, it may be obtained directly by measuring the TOC in the sample or by subtracting the total IC from the TC. Represented formulaically:

$$TOC=TC-IC$$

The amount of TOC can alternatively be measured by detecting and recording the amount of POC plus the amount of NPOC. POCs are volatile and semi-volatile organic materials that have been sparged from the sample. Generally, however, POCs constitute less than 1% of the TC in a given sample. Represented formulaically:

$$TOC=POC+NPOC$$

Carbon analysis may be conducted by oxidizing a carbon containing sample to water and $CO_2$. A sample may be oxidized using an oxidation analyzer such as a wet chemical oxidation analyzer or a combustion oxidation analyzer, for example.

Wet chemical oxidation analyzer oxidizes a sample by subjecting it to a chemical substance such as persulfate while bombarding the sample with ultraviolet (UV) radiation. This reaction produces $CO_2$ gas. As $CO_2$ gas is produced from this reaction, a stream of inert gas may be employed to sweep the $CO_2$ gas into a $CO_2$ detector. Nitrogen may be used as the inert gas. One such wet chemical oxidation analyzer is the Fusion TOC™ analyzer available from the present assignee, Teledyne Tekmar Company out of Cincinnati, Ohio.

A combustion oxidation analyzer subjects the sample to an elevated temperature, sometimes as high as about 1000 degrees Celsius to oxidize the sample. One such combustion analyzer is the Apollo 9000™ Combustion TOC Analyzer also available from the present assignee, Teledyne Tekmar Company. Both the wet chemical oxidation and the combustion oxidation analytical methods, provide a theoretically complete oxidation of the carbon in the sample.

Once the carbon in the sample is oxidized to $CO_2$ gas, the amount of carbon constituent element may be detected and measured in a $CO_2$ detector portion of the analytical instrument. One type of $CO_2$ detector may be a Non-Dispersive InfraRed detector (NDIR) to measure the $CO_2$ content in a gas sample. An NDIR detector focuses on the absorption frequency of carbon and provides a signal proportional to the instantaneous concentration of carbon in the carrier gas. This output signal may be linearized. Discrete samples of the $CO_2$ gas are transferred from a UV reactor to the NDIR detector under pressures exceeding atmospheric pressures. The static trapped and pressurized $CO_2$ gas sample may be subjected to multiple measurements in the NDIR detector. The NDIR signal is measured and is referred to stored calibration data so that the concentration of the carbon constituent element in the sample is calculated to determine the carbon concentration of the sample in parts-per-million (ppm), parts-per-billion (ppb) or lower. Further description of an NDIR detector may be found in U.S. Pat. No. 5,835,216 to Koskinen titled "METHOD OF CONTROLLING A SHORT-ETALON FABRY-PEROT INTERFEROMETER USED IN AN NDIR MEASUREMENT APPARATUS", which is incorporated herein by reference.

FIG. 1 illustrates a flow diagram of one embodiment of an analyzer 100. The analyzer 100 may comprise a reactor 119 and a detector 180. The reactor 119 is coupled to the detector 180. The analyzer 100 including the detector 180 may be pressurized. The analyzer 100 may be implemented to analyze dissolved carbon to measure the carbon content of a sample. The analyzer 100 also may comprise a motor-driven syringe pump 102 connected to a primary port 104 of a multi-port valve 106.

In one embodiment, the syringe pump 102 may be employed to deliver a sample to the analyzer 100. The syringe pump 102 dispenses a sample into the reactor 119 where dissolved organic elements or compounds are converted into a gas. In the case where the sample comprises carbon, the syringe pump 102 dispenses the carbon containing sample into the reactor 119 where it is dissolved and converted into gaseous $CO_2$, for example. The analyzer 100 may comprise a variety of reactors such as wet chemical oxidation (UV) or combustion oxidation type reactors. The syringe pump 102 may be employed to deliver relatively small volumes (e.g., from about 1 µl to about 2.5 ml) of the samples of interest as may be needed in certain types of reactors (e.g., combustion reactors). The syringe pump 102 may be adapted to deliver relatively high volumes (e.g., from about 25 ml to about 100 ml) of the samples of interest as may be needed in UV or UV/persulfate or heated/persulfate type of reactors. UV reaction chambers may accept larger volumes (e.g., up to about 16 ml) of the sample of interest and thus permit measurement of lower concentrations of dissolved carbon in the sample.

In the illustrated embodiment, the reactor 119 is a UV-reactor 119 and the syringe pump 102 is capable of delivering fluids to the reactor 119. The syringe pump 102 is a precision measuring instrument that aspirates and dispenses fluids. A motor (not shown) drives a valve actuator and a syringe plunger to allow the syringe pump 102 to dispense a known quantity of fluid. The fluid may comprise a sample, reagent, oxidant, acid, rinsing solution and the like.

In one embodiment, the multi-port valve 106 comprises eight ports: A, B, C, D, E, F, G and H, and is operable to fluidically couple the primary port 104 to any one of the other ports (A-H). The multi-port valve 106 may comprise additional or fewer ports without limiting the scope of the analyzer 100. When the primary port 104 couples to one of the ports A-H the rest of the ports A-H are isolated from each other and from the primary port 104. The multi-port valve 106 can be actuated pneumatically, electrically or in any suitable manner with both clockwise and counterclockwise action. As indicated in the illustrated embodiment, the multi-port valve 106 may be an 8-port valve available from Kloehn Co. Ltd., Las Vegas, Nev. Other suitable single port or multi-port valves may be employed without limiting the scope of the analyzer 100.

Each port A-H of the multi-port valve 106 has inputs for specific items so as to avoid cross-contamination. For example, port A of the multi-port valve 106 may be reserved for acid, whereas port H may be reserved for an oxidant such as persulfate. The ports A-H are described below.

Port D of the multi-port valve 106 couples to a sample inlet 108 over a line 110. The sample inlet 108 receives a sample 112 of interest to be analyzed. The sample 112 may be provided individually or in an auto-sampler (ASM) that holds many other samples of interest, for example.

Port C couples to a sparging chamber 114 of an IC sparger 115 over a line 116. In the sparging chamber 114, dissolved IC and POCs can be removed from the sample by adding acid to the sample and sparging the resulting mixture. The IC sparger 115 may be a glass vessel that holds the sample while the instrument purges the IC and POC from the sample while preparing the sample for TOC analysis.

Port B couples to a reaction chamber 118 of the reactor 119 over a line 120. In one embodiment, the reaction chamber 118 may comprise a UV source 122 to convert organic carbon in the sample into carbon gas (e.g., gaseous $CO_2$). A reagent 124 may be provided in the reaction chamber 118 along with the sample to accelerate the reaction. The reactor 119 may be a glass vessel comprising the UV source 122. The analyzer 100 causes both the sample and the reagent 124 to react and, when combined with the UV rays, oxidizes the carbon in the sample.

Port A couples to an acid inlet 126 over a line 128. The acid inlet 126 receives acid from a reservoir of acid 130, preferably a 25% solution of phosphoric acid ($H_3PO_4$).

Port H couples to the reagent 124 at inlet 132 over a line 136. The reagent inlet 132 receives a reagent, e.g., an oxidant, from a reservoir of reagent 124, preferably 10% sodium persulfate ($Na_2S_2O_8$), but 2% or 3% potassium persulfate ($K_2S_2O_8$) also can be used. The reagent 124 preferably also includes about 5% phosphoric acid. The persulfate/acid mixture of the reagent 124 may be used in the reaction chamber 118, whereas the acid 130 by itself may be used in the sparging chamber 114. One purpose for this separation is to maintain good sparging efficiency in both the sparging chamber 114 and the reaction chamber 118. Unlike the reaction chamber 118, the sparging chamber 114 does not include a UV source to break down persulfate. Residual persulfate can cause a precipitate to slowly build up on surfaces in the chamber, including the glass frit used as a disperser. Such build-up can clog portions of the frit, gradually degrading sparging efficiency.

Port G couples to a rinse solution 138 at inlet 134 over a line 137. The rinse solution inlet 134 receives the rinse solution 138 such as de-ionized water.

Port F couples to a waste 141 at outlet 140 over a line 142.

Port E as shown is unused.

With the syringe pump 102 and the multi-port valve 106 oriented vertically as shown, it is possible for minute portions (microliter levels) of liquid residue in the upper ports A, H, B, G to fall into the syringe pump 102, causing contamination. Therefore, the acid 130, reagent 124 and rinse solution 138 may couple to the adjacent upper ports G, H, A because these liquids 130, 124, 138 have low and consistent carbon concentrations which are measurable. The sample 112, on the other hand, connects to a downward-facing port D to avoid such contamination. In the illustrated embodiment, the sparging chamber 114 and the UV reaction chamber 118 may couple to the adjacent ports B, C between the sample port D and the ports A, H, G used for the liquids 130, 124, 138. This arrangement, coupled with the bidirectional capability of the multi-port valve 106, minimizes valve movement during operating procedures described below and minimizes contamination. The embodiments, however, are not limited in this context.

The analyzer 100 also comprises a carrier gas inlet 144 to receive a pressure regulated carrier gas source 146 such as nitrogen, for example, or what is known in the art as ultra-zero air. Lines 148a-e, 152a-c, 154, T-connection 150, electrically controlled on/off valves 156, 158, flow restrictor 160, pressure regulator 162 and mass flow controller 164 are connected (or coupled) as shown to permit the carrier gas delivered by the carrier gas source 146 to be routed to the sparging chamber 114 and to a sparge tube 168 of the reaction chamber 118. The sparge tube 168 may be made of glass having a standard glass frit (not shown in FIG. 1) affixed at the bottom thereof as is known in the art to disperse the carrier gas evenly through the sample and avoid channeling. The pressure regulator 162 may be adjusted to provide, for example, a predetermined flow of about 200 ml/min, for example, through the vent of the valve 172. To measure the flow in the analyzer 100, the valve 172 is turned off and the valve 156 is turned on.

A line 170a carries gasses away from the sparging chamber 114 to an electrically controlled 3-port valve 172. Likewise, a line 174a carries gasses away from the UV chamber 118 to a valve 176 which is similar to the valve 172. In an "off" state, the valves 172, 176 connect a common "C" port to a normally open "NO" port while a normally closed "NC" port is isolated. In an "on" state, the C port connects to the NC port and the NO port is isolated. Gas from the sparging chamber 114 can thus be vented via a line 170b or sent to a $CO_2$ detector via a line 170c, depending on the state of the valve 172. In like manner, gas from the UV chamber 118 can be vented over a line 174b or sent to a $CO_2$ detector over a line 174c. The lines 170c, 174c meet at a T-connection 178. As illustrated, gas flows from the T-connection 178 to a $CO_2$ detector 180 via lines 182a-d, a mist trap 186, a permeation tube 188 and a scrubber 190.

In one embodiment the detector 180 may be a NDIR or other suitable $CO_2$ detector that is capable of being pressurized. In various other embodiments, the detector 180 may be employed to detect other elements and/or compounds. For example, the detector 180 may be used to detect carbon (C), sulfur (S), nitrogen (N) and other constituent elements in various compounds. The detector 180 may employ various technologies to detect these constituent elements such as chromatography, chemiluminescence, radiated energy (e.g., infra-red or ultraviolet absorption), among others. These constituent elements each absorb a unique spectrum (e.g., radiated energy at a specific wavelength). These constituent elements also may have a unique chromatographic and/or chemiluminescent signature. In the illustrated embodiment, the detector 180 is implemented as an NDIR detector. Gas from the detector 180 may be vented through line 182e and a valve 196. Waste from the mist trap 186 may be drained through a line 197 and a valve 198.

In one embodiment, the detector 180 may have a linearized output to provide a linearized signal indicative of the amount of $CO_2$ in the gas sample over an electrical line 192 to a computer 194 adapted to communicate with the analyzer 100. The computer 194 may be a controller or processor and in one embodiment may be a dedicated controller or processor that resides in the analyzer 100. The computer 194 also controls the valves 106, 156, 158, 172, 176, 196, 198 and the syringe pump 102 to execute the various methods of operation. The computer 194 may be remotely connected to the detector 180 over any suitable wired or wireless network.

The mist trap 186 and the permeation tube 188 form a moisture control system that may be implemented with standard components and function to remove water vapor from the gas stream. Water vapor is undesirable because it can interfere with the $CO_2$ measurement. The mist trap 186 removes water vapor by trapping the mist and the permeation tube 188 dries the gas prior to its entering the detector 180. Removing water vapor from the $CO_2$ is a factor in preserving the reliability and sensitivity of the analysis. Condensation removal occurs by way of methods and tubing that are well known in the art.

In one embodiment, the scrubber 190 may be implemented as a halogen scrubber to remove chlorine and other halogens from the $CO_2$ gas before it enters the detector 180 as such substances may damage the detector 180. The scrubber 190 may comprise a U-shaped tube filled with glass or pyrex wool and tin and copper granules (beads) to capture halogens as the $CO_2$ gas flows through these materials. The tin granules may be sandwiched between Pyrex brand wool plugs in one arm 191a of the "U" and a quantity of copper granules sandwiched between like plugs in the other arm 191b of the "U". The scrubber 190 removes chlorine from the $CO_2$ gas stream by reaction with the copper and tin granules. Chlorine is undesirable because it also can interfere with the $CO_2$ measurement and also may harm the detector 180. Discoloration of the copper granules, which are disposed upstream of the tin granules, provides an indication that the scrubber 190 should be replaced.

Carrier gas also may be supplied to the sparging chamber 114 through lines 148a-e, a pressure regulator 162, a flow restrictor 160 and the valve 156. Carrier gas also may be supplied to the sparging chamber 114 through lines 152a-b, 154, 148e, a mass flow controller 164 and the valves 156, 158. Carrier gas also may be supplied to the sparge tube 168 of the UV reaction chamber 118 through lines 152a-c, the mass flow controller 164 and the valve 158.

The mass flow controller 164 has an inlet port 165, an outlet port 167, a mass flow sensor (not shown), a pressure transducer (not shown), and a proportional control valve (not shown). The mass flow controller 164 is fitted with a closed loop control system which is given an input signal either by an operator, an external circuit/computer or the computer 194. The mass flow controller 164 compares the input signal to the value from the mass flow sensor and adjusts the proportional valve accordingly to achieve the required flow. The flow rate is specified as a percentage of its calibrated full scale flow rate and may be supplied to the mass flow controller 164 as a voltage, current or other electrical signal. The mass flow controller 164 generally requires the carrier gas from the source 146 to be within a predetermined pressure range. In one embodiment, the pressure at the input of the mass flow controller 164 is in the range of about 80-100 psig. The mass flow controller 164 may be used to measure and control the flow of gases in the analyzer 100. The mass flow controller 164 sets the system operating pressure at its outlet port 167. The mass flow controller 164 controls the flow through the outlet port 167 until the system pressure reaches the set operating pressure. When the system reaches the operating pressure, the flow through the mass flow controller 164 is cut-off and the system pressure is held static. Measurements of the constituent contained in the gas sample are performed under static system operating pressure, as discussed in more detail below. The mass flow controller 164 may be calibrated to control a specific type of gas, e.g., Nitrogen, at a particular range of flow rates. The mass flow controller 164 may be given a set-point from 0 to 100% of its full scale range but may typically be operated in the 10 to 90% of full scale range where the best accuracy may be achieved. The mass flow controller 164 then controls the flow rate to the given set-point. The mass flow controller 164 may be either analog or digital. A digital mass flow controller is usually able to control more than one type of gas whereas an analog controller may be limited to the gas for which it was calibrated. The embodiments, however, are not limited in this context.

The pressure regulator 162 may be employed to control the flow through the flow restrictor 160. The pressure regulator 162 may be set manually or automatically under the control of the computer 194 or an external controller.

The flowpath of the analyzer 100 is greatly simplified compared to conventional dissolved carbon analyzers, particularly UV-reactor 119 type analyzers, by making effective use of the syringe pump 102 and the multi-port valve 106. The single multi-port valve 106, by virtue of its multiplicity of ports selectively coupleable to the primary port 104, connects the syringe pump 102 to each of seven different inlets, chambers or outlets. Accordingly, additional valves may not be required in the liquid handling path.

The components of the analyzer 100 shown in FIG. 1 may be arranged in or on an analyzer cabinet or other suitable housing. The syringe pump 102, the multi-port valve 106, the sparging chamber 114, the UV chamber 118, the mist trap 186 and the scrubber 190 may be mounted on a front panel of the analyzer cabinet for ease of viewing to verify operation. The valves 106, 156, 158, 172, 176, the flow restrictor 160 and the T-connections 150, 178 may be mounted elsewhere in the analyzer cabinet. Each of the lines that interconnect the various components of the analyzer 100 (i.e., lines 116, 120, 148a-e, 152a-c, 170a-c, 174a-c, 182a-e, 197) may be a length of flexible tube and may be of Teflon brand polymer and generally of small size (0.125 or 0.0625 inch outside diameter [O.D.]).

Embodiments of the analyzer 100, particularly dissolved carbon analyzers employing UV, UV/persulfate or heated/persulfate oxidation techniques may comprise multiple valves, connections and tubing connected together in any suitable arrangement to form lines 116, 120, 148a-e, 152a-c, 170a-c, 182a-e and 197. The analyzer 100 may employ different types of tubes for interconnections. The different types of tubes have appearances that differ from one another. The tubes may be color-coded to signify their function in the flow path. For example, blue tubes may be used for lines that carry fluids exclusively to or from the UV chamber 118 and red tubes can be used for lines that carry fluids exclusively to or from the sparging chamber 114. Yellow tubes can then be used for all other lines.

Figure 2A:
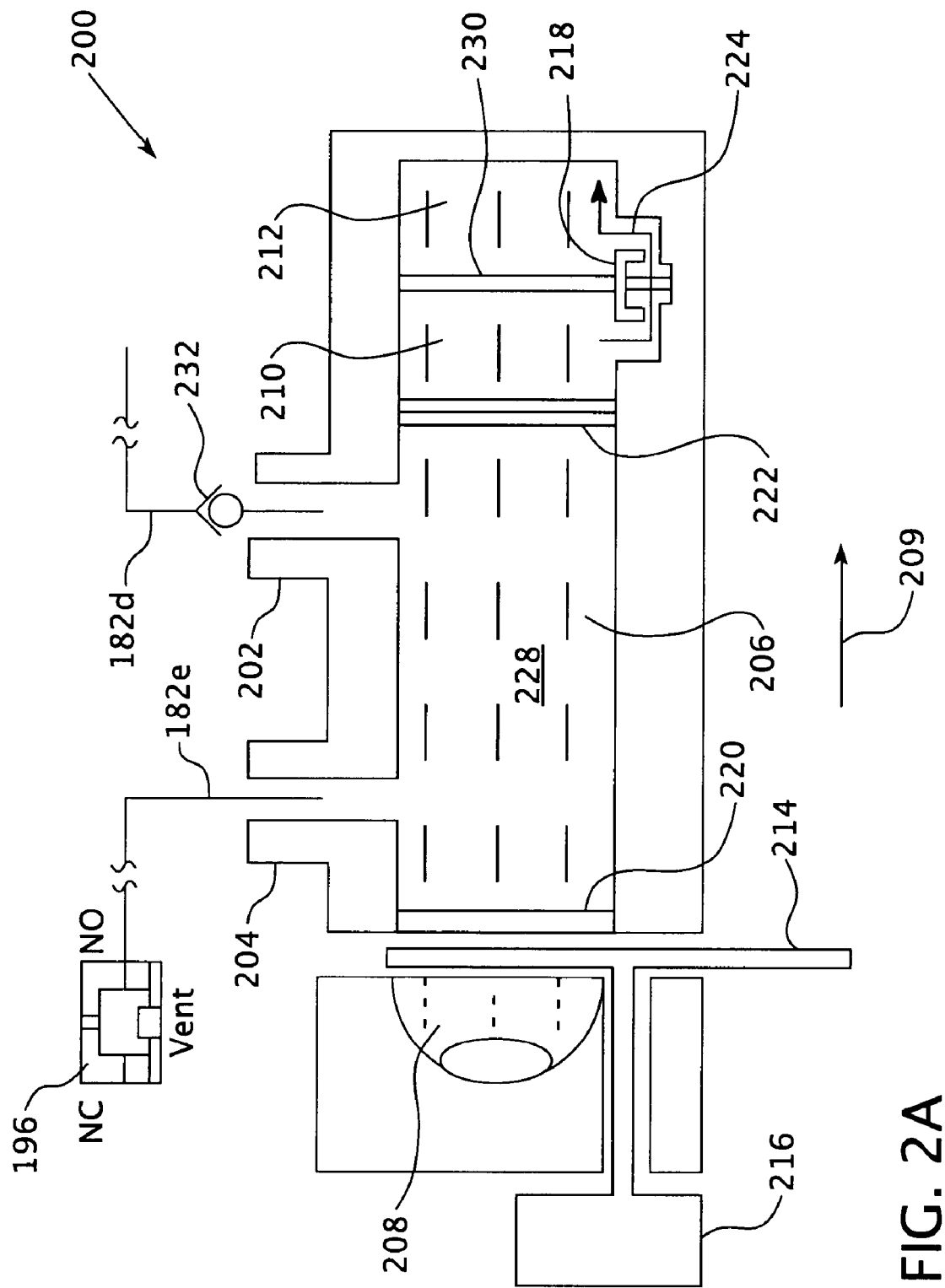
FIG. 2A illustrates a cross-sectional schematic diagram of one embodiment of a detector.

FIG. 2A illustrates a cross-sectional schematic diagram of a detector 200. The detector 200 is one embodiment of the detector 180. The detector 200 comprises a sample cell 206, first and second detector cells 210, 212 located adjacent to the sample cell 206, and a radiant energy source 208 optically coupled to the sample cell 206 and to the first and second detector cells 210, 212. The detector 200 employs radiant energy such as electromagnetic radiation to measure a constituent in a gas sample. A beam of radiant energy has a specific wavelength and is directed through a pressurized gas sample in the sample cell 206. The specific wavelength is selected so that it is absorbed by a constituent of the sample of interest. The amount radiation at the specific wavelength that is absorbed by the constituent directly correlates to the amount of the constituent present in the sample cell 206. The constituent may be any desirable element, and thus, the radiant energy source 208 may be selected to output a beam of radiant energy having a specific wavelength that may be suitably absorbed by the constituent of interest. For example, constituents such as carbon (C), sulfur (S), nitrogen (N), among other constituent elements, each absorb a different specific wavelength. Therefore, to measure the amount of a constituent contained in a pressurized gas sample, a radiant energy source 208 that emits a suitable specific wavelength should be employed.

The sample cell 206 comprises an inlet 202 coupled to the line 182d and an outlet 204 coupled to the line 182e. The sample cell 206 comprises first and second windows 220, 222 suitable to pass the radiant energy. Accordingly, the sample cell 206 is optically coupled to the first detector cell 210. The sample cell 206 defines a chamber 228 therein having a predetermined volume, which is suitable to receive a mass quantity of a gas sample to be measured under system operating pressure as set and controlled by the mass flow controller 164. In the embodiment illustrated in FIG. 2A, the system operating pressure of the detector 200 may be determined by the thickness and/or strength of the first and second windows 220, 222 materials. Thus, the first and second windows 220, 222 may be formed of a suitable thickness and/or material to enable its operation under various system operating pressures.

The first and second detector cells 210, 212 are located adjacent to the sample cell 206 and are separated by the second window 222. The first and second detector cells 210, 212 are fluidically coupled. However, the first and second detector cells 210, 212 are fluidically isolated from the sample cell 206. The first and second detector cells 210, 212 are filled with a predetermined gaseous quantity of a constituent element similar to the constituent element of interest in the gas sample to be measured. For example, if the constituent is carbon, then the first and second detector cells 210, 212 may be filled with a gaseous quantity of carbon; if the constituent is sulfur, then the first and second detector cells 210, 212 may be filled with a gaseous quantity of sulfur; if the constituent is nitrogen, then the first and second detector cells 210, 212 may be filled with a gaseous quantity of nitrogen; and so on. A wall 230 separates the first and second detector cells 210, 212. A flow sensor 218 is located between the first and second detector cells 210, 212 and provides an opening to enable flow of the constituent gas contained therein to occur therebetween as a result of any pressure changes between the first and second detector cells 210, 212. The rate of flow between the first and second detector cells 210, 212 is proportional to the amount of radiation from the radiant energy source 208 that is absorbed by the gaseous constituent in the first detector cell 210.

A radiant energy source 208 is located adjacent to the first window 220 to emit a beam of incident radiation along the direction indicated by arrow 209 on the gas sample in the sample cell 206. The energy passes through the first window 220 into the sample cell 208 and through the second window 222 into the first detector cell 210. A rotating chopper blade 214 driven by a motor 216 is located in front of the radiant energy source 208 and interrupts the energy at predetermined regular intervals. The interruption of the energy causes changes in the energy reaching the first detector cell 210. Pulsating the energy causes a pulsing of pressure in the first detector cell 210 and creates a flow through the flow sensor 218 between the first and second detector cells 210, 212 as indicated by arrow 224. The rate of flow through the flow sensor 218 is proportional to the amount of radiation absorbed by the constituent in the first sample cell 210. The flow sensor 218 emits an electrical signal proportional to the magnitude of the flow. When the chamber 228 of the sample cell 206 is empty a maximum amount of radiant energy reaches the first detector cell 210 and a maximum flow access through the flow sensor 218.

To conduct a measurement, the valve 196 is closed in order to receive a mass quantity of the gas sample in the chamber 228 of the sample cell 206 while the analyzer 100 is being pressurized to the system operating pressure by the mass flow controller 164. Thus, while the analyzer 100 is being pressurized by the mass flow controller 164, the chamber 228 of the sample cell 206 fills with the gas sample of interest and over a predetermined period of time, substantially all of the mass of the gas sample in the analyzer 100 is contained in the chamber 228 of the sample cell 206. Once the predetermined time has elapsed and the analyzer in under the set operating pressure, the mass flow controller maintains the analyzer, including the sample gas contained in the chamber 228 of the sample cell 206 under operating pressure to conduct the measurement. Accordingly, the radiant energy source 208 emits radiant energy at a predefined wavelength which may be selected according to the constituent to be measured. A quantity of the constituent contained in the chamber 208 will absorb a portion of the radiated energy proportionally to the quantity or mass of the constituent. The constituent in the gas sample absorbs some of the radiant energy that would otherwise pass through to the first detector cell 210. The pulsating radiant energy that is not absorbed by the constituent reaches the first detector cell 210 and causes a pressure difference between the first detector cell 210 (higher pressure) and the second detector cell 212 (lower pressure). The difference in pressure causes a change in flow between the first and second detector cells 210, 212. The more energy is absorbed by the constituent, the less energy reaches the first detector cell 210 and, therefore, the lower the flow between the first and second detector cells 210, 212. The less energy is absorbed by the constituent, the more energy reaches the first detector cell 210 and, therefore, the higher the flow between the first and second detector cells 210, 212. Therefore, the flow rate between the first and second detector cells 210, 212 is inversely proportional to the quantity of the constituent element of interest contained in the pressurized gas sample in the sample cell 206. Accordingly, the change in flow between the first and second detector cells 210, 212 correlates to the amount of the constituent element in the gas sample. After completing a suitable number of flow measurements, the pressurized gas sample in the sample cell 206 may be purged through the outlet 204 by opening the valve 196 to vent the pressurized gas sample out of the chamber 228. Accordingly, the flow sensor 218 output signal decreases to its previous "empty chamber 228" level. The area defined by the electrical signal output of the flow sensor 218 over time is the raw data that may be analyzed to determine the amount of constituent contained in the pressurized gas sample.

It will be appreciated that the radiant energy source 208 may be selected to emit energy of a predetermined wavelength in any portion of the electromagnetic spectrum based on the constituent to be analyzed. In other words, the wavelength of the energy may be selected so as to coincide with a particular sorption process for a constituent to be analyzed. The wavelength of the radiant energy may be selected, for example, from extreme ultraviolet of about 10 nm to far infrared of about 1 mm, for example. Furthermore, the sample cell 206 may be adapted to receive gas samples at various predetermined pressures above atmospheric pressure. The gas pressure may be selected according to a desired sensitivity of the measurement, for example, among the selection criteria. The embodiments, however, are not limited in this context.

In one embodiment, the detector 200 may be used to measure a mass quantity of carbon constituent in a pressurized $CO_2$ gas sample. The sample cell 206 is pressurized to the operating pressure by the mass flow controller 164. To initiate the measurement, the outlet 204 of the sample cell 206 is closed, e.g., the valve 196 is closed and the sample cell 206 receives pressurized $CO_2$ gas outflow from the UV reactor 119 (FIG. 1) or the IC sparger 115 (FIG. 1) through the gas inlet 202 through line 182d. A check valve 232 may be located at the gas inlet 202 to prevent backflow of the pressurized $CO_2$ from the inlet 202. The pressurized $CO_2$ gas may be purged from the detector 200 through the outlet 204 through line 182e after the measurement by opening the valve 196 to vent. In one embodiment, the radiant energy source 208 is an infrared energy source to generate a beam of energy in the infrared wavelength along the direction indicated by arrow 209. The beam of infrared energy passes through the first window 220 on one end of the sample cell 206 and is incident on the pressurized $CO_2$ gas sample to be measured for carbon constituents. The infrared energy passes through the pressurized $CO_2$ sample. Some of the infrared energy may be absorbed by the pressurized $CO_2$ gas sample and the rest of the infrared energy passes through the second window 222 to the first detector cell 210. The first and second detector cells 210, 212 are sealed from the sample cell 206 and are filled with $CO_2$ gas. The first and second detector cells 210, 212 are isolated from the sample cell 206 by the cell window 220. The cell window 220, however, permits the infrared energy beam to pass through to the first detector cell 210.

The detector 200 operates by emitting a single beam of infrared energy through a static pressurized $CO_2$ gas sample contained in the sample cell 206. The beam then hits the first detector cell 210 filled with $CO_2$ gas. The energy beam, however, is interrupted by the rotating chopper 214 driven by the motor 216 and results in a pulsed beam of infrared energy. The pulsed beam results in a different amount of energy reaching the first detector cell 210, which results in a pulsing of pressure and flow in the direction indicated by the arrow 224 through the mass type flow sensor 218 located between the first and second detector cells 210, 212. The mass flow sensor 218 emits an electrical signal (e.g., millivolts [mV]) that is proportional to the magnitude of the flow therethrough. When no $CO_2$ is present in the sample cell 206, the maximum amount of energy is available to enter the first detector cell 210 and the flow between the first and second detector cells 210, 212 is at its maximum. As previously discussed, in the embodiment illustrated in FIG. 2A, the system operating pressure of the detector 200 may be determined by the thickness and/or strength of the first and second windows 220, 222 materials. Thus, the thickness and/or material of the first and second windows 220, 222 may be selected based on the system operating pressure.

If $CO_2$ is present in the sample cell 206, it absorbs some of the infrared energy that would otherwise enter the first detector cell 210, thus reducing the pressure in the first detector cell 210. This results in a reduction of flow between the first and second detector cells 210, 212. When the $CO_2$ is purged from the sample cell 206, the signal strength between the first and second detector cells 210, 212 returns to its previous empty sample cell 206 level.

Figure 2B:
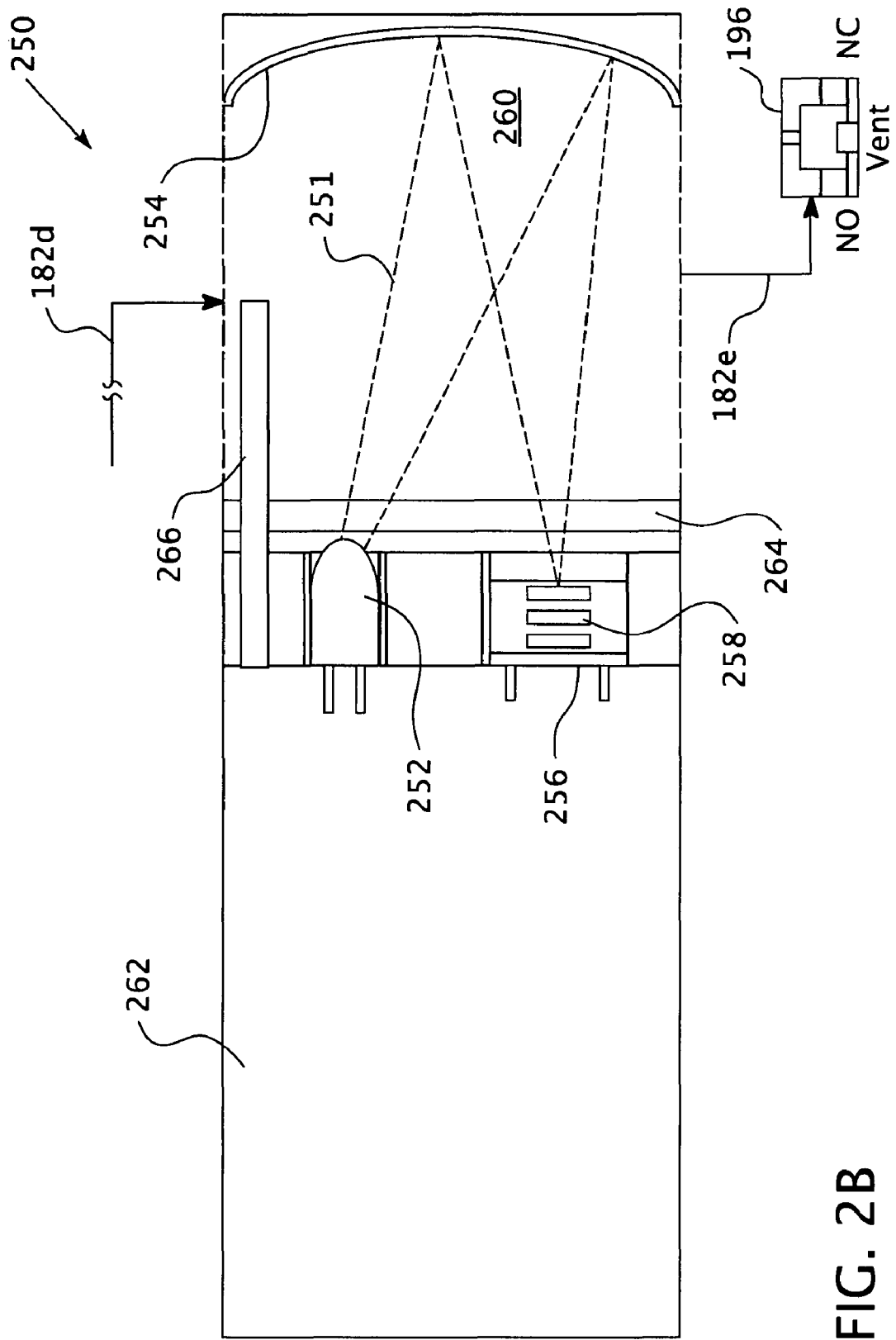
FIG. 2B illustrates a cross-sectional schematic diagram of one embodiment of a detector.

FIG. 2B illustrates a cross-sectional schematic diagram of a detector 250. The detector 250 is one embodiment of the detector 180. The detector 250 comprises a housing 262, a detector cell 260, and various components such as a lamp 252 to emit radiant energy 251, a mirror 254 to reflect the radiant energy to an IR detector 256. A window 264 separates the lamp 252 and the IR detector 256 from the detector cell 260. In one embodiment, the window 264 may be a sapphire window. A temperature sensor 266 is provided to measure the temperature in the detector cell 260. The detector 250 may be used to measure the amount of $CO_2$ in the sample 112 to determine the carbon content in the sample 112. As previously described, the analyzer 100 converts carbon in the sample to $CO_2$ gas. The detector 250 may be an NDIR single-beam, dual-wavelength infrared detector that uses no moving parts to measure this $CO_2$. As previously discussed, the measurement of the $CO_2$ is proportional to the carbon in the sample 112 introduced into the analyzer 100.

Inside the detector 250, light in the form of infrared energy 251 from an electronically pulsed miniature lamp 252 is reflected from the minor 254 and re-focused back to the IR detector 256. The mirror 254 may be gold plated and coated. The IR detector 256 is located behind a silicon-based Fabry-Perot Interferometer 258 (FPI). This miniature FPI 258 is electronically tuned so that its measurement wavelength is converted between the absorption band of the $CO_2$ gas and a reference band. When the FPI 258 passband coincides with the absorption wavelength of the $CO_2$ gas, the IR detector 256 experiences a decrease in the light transmission. The measurement wavelength of the FPI 258 is then changed to the reference band (that has no absorption lines) and the IR detector 256 experiences a full light transmission. The degree of light absorption in the $CO_2$ gas, indicated by the ratio of the two absorption band and reference band signals, is proportional to the $CO_2$ gas concentration. $CO_2$ shows a unique adsorption spectrum when infrared energy 251 passes through it, allowing the NDIR detector 250 to distinguish it from other gases.

Pressurized detection, or static read, is a technique used for concentrating substantially all of the $CO_2$ produced by the oxidation of the sample in the analyzer 100 as previously discussed. The technique can be used for both qualitative and quantitative analysis. Some pressurization techniques will now be described.

Using conventional NDIR technology, the measurements are performed by oxidation of the specific carbon component by UV/Persulfate oxidation to create $CO_2$, which is swept through an NDIR detector. In this technique, the adsorption of the infrared light is measured over time as the $CO_2$ is swept through the conventional NDIR detector. The resulting measurement correlates to a peak, which can be integrated and correlated to a concentration.

Employing the detector 250 in a pressurized detection technique, or static read, allows for the specific carbon component to be oxidized and the resultant $CO_2$ to be swept into the detector 250 at the inlet port 182d using a non-interfering, inert gas, which is metered by the mass flow controller 264. The valve 196 located at the outlet port 182e of the detector prevents the escape of any of the CO2 from the detector 250. A single measurement can be made to determine the amount of $CO_2$ in the detector cell 260. The reading correlates directly to the concentration of the carbon contribution from the sample 112.

An inherent advantage of this technique is that all of the $CO_2$ is in the detector cell 260 at the same time for the detector 250 measurement. With all of the $CO_2$ in the detector cell 260, the sensitivity of the analysis is significantly increased.

Another advantage of this application is that there is one measurement made that represents the concentration of $CO_2$ in the detector cell 260 versus multiple measurements made in flow-through designs over time that result in a peak. Because this technique is a static read, it eliminates the inherent error that is associated with time delays between measurements employed in conventional flow-through technology. These time delays add error to the integration of the $CO_2$ peak. The elimination of this error allows for lower detection limits and increased precision.

The static read of the detector 250 is accomplished by pressurizing the detector cell 260 with a carrier gas, which contains the $CO_2$ from the oxidized sample 112. The pressure required for static read is generally between 30-60 psig. Although, as previously discussed, other pressures may be used, in one embodiment, the detector 250 pressure may be set to about 50 psig.

Figure 2C:
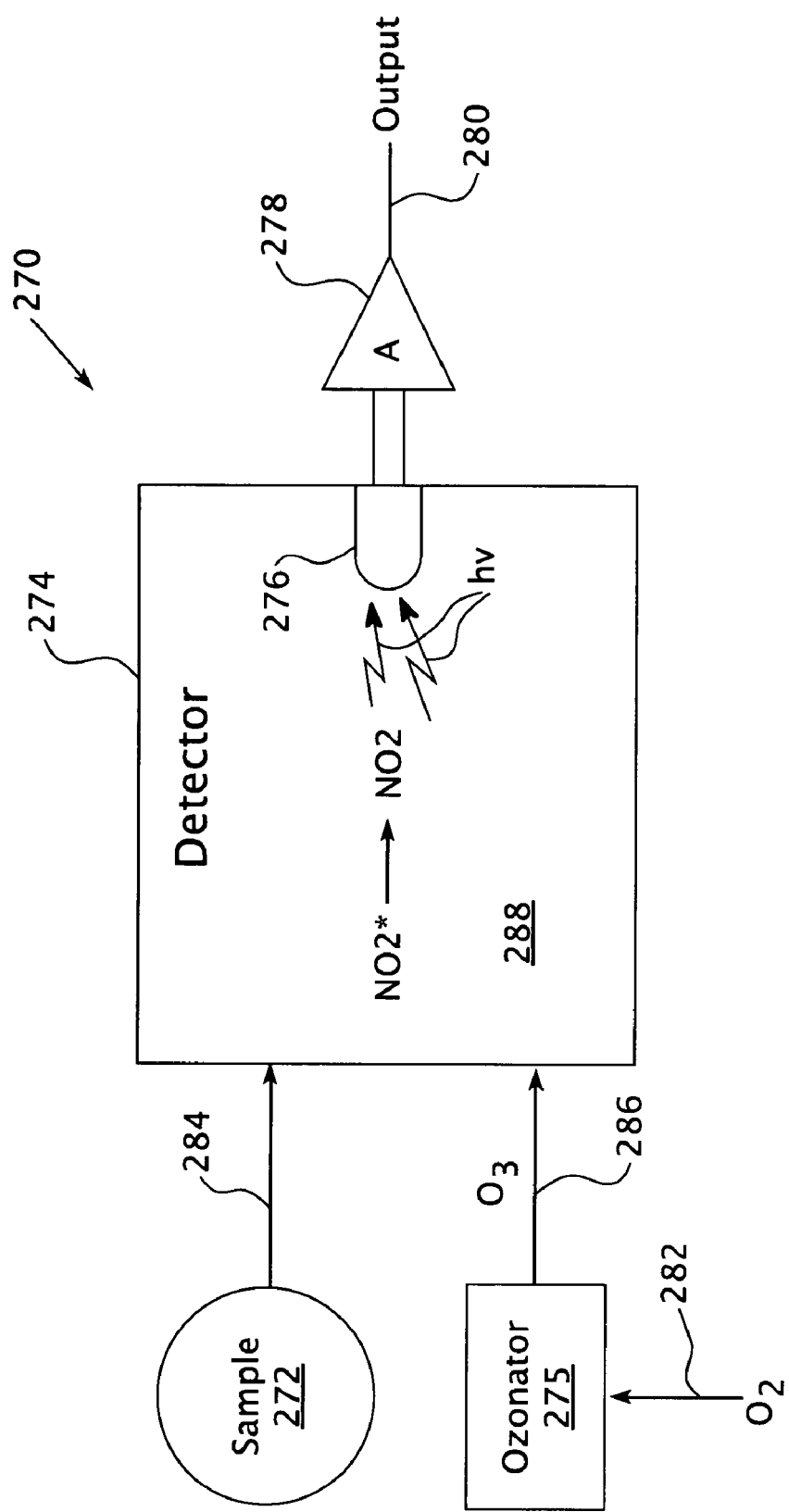
FIG. 2C a schematic diagram of one embodiment of a chemiluminescence detection system.

FIG. 2C illustrates a schematic diagram of one embodiment of a chemiluminescence detection system 270. The chemiluminescence detection system 270 comprises a chemiluminescence detector 274. Chemiluminescence detector 274 receives a pressurized nitric oxide (NO) gas sample 272. The sample 112 (FIG. 1) may be injected in a combustion furnace where the nitrogen (N) in the sample 112 is converted to NO while carbon is converted to CO2. A mass flow controller may be employed to pressurize the NO gas sample 272 in a manner similar to that discussed above with respect to the analyzer 100 (FIG. 1), the detector 200 (FIG. 2A), and the detector 250 (FIG. 2B). The carrier gas sweeps the sample gas 272 into the non-dispersive infrared detector (NDIR) (e.g., the detectors 200, 250) where the concentration of CO2 in the sample gas 272 is measured. The pressurized NO gas sample 272 is then delivered to the chemiluminescence detector 274 via a line 284. Oxygen ($O_2$) is fed to an ozonator 275 via a line 282. The ozonator 275 converts the $O_2$ into ozone $O_3$ and provides it to the chemiluminescence detector 274 via a line 286. Inside the chemiluminescence detector 274, the pressurized NO gas sample 272 is mixed with the $O_3$. This reaction yields an excited nitrogen dioxide ($NO_2^*$). When the $NO_2^*$ returns to its ground state $NO_2$, it gives off the extra energy in the form of light hv. This process is known as chemiluminescence. The light hv given by the chemiluminescence can be utilized for analyzing the NO or NOX concentration within the pressurized gaseous sample 272.

In the NO mode, the chemiluminescent reaction occurs between the O3 and the NO yielding $NO_2^*$ and oxygen. This reaction produces light hv. The intensity of th light hv is linearly proportional to the mass of the pressurized NO in the reaction chamber 288. A light-detecting device 276 (e.g., a photodiode) converts the light signal hv to an electrical output signal 280 that allows quantitation. In one embodiment, the ligh-detecting device 276 may be a chemiluminescence photodiode detector (CLD), for example. The amount of light hv detected is directly proportional to the amount of NO in the gas sample 272. The light hv measured with the light-detecting device 276 and associated amplification electronics 278 produce the electrical output signal 280. The light-detecting device 276 is thermoelectrically cooled and temperature regulated. Formulaically, the reaction may be expressed as:

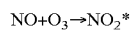

For $NO_x$ detection, NO plus $NO_2$ is determined as discussed above, however, the sample 272 is first routed through a $NO_2$ to NO converter, which converts the $NO_2$ in the sample 272 to NO. The resultant chemiluminescent $NO-O_3$ reaction is then directly proportional to the total $NO_x$ concentration.

The total N in the sample 112 (FIG. 1) may be measured in combination with the TC in the sample 112. For example, catalytic combustion of the sample 112 may be employed to convert all forms of N in the sample 112 to NO and C in the sample 112 to $CO_2$. The concentration of $CO_2$ content may be measured as discussed above with respect to FIGS. 1, 2A, and 2B. The concentration of NO may be determined as discussed with respect to FIG. 2C. The result may be presented in units of mass C and/or N per volume or mass of sample 112.

Having described the various components of the analyzer 100, the operation of the analyzer 100 is now described with reference to FIGS. 1 and 2A, 2B. The sample 112 is received from a sample vial and sent to the reactor 119. The reactor 119 comprises a reagent for oxidation of a component of the sample 112 to a gas, e.g., carbon to $CO_2$. The valve 196 is closed and $CO_2$ is sparged from the reactor 119 into the NDIR detector 180. The check valve 232 may be located on the inlet 202 of the NDIR detector 180 to prevent any $CO_2$ gas from back flowing out of the detector 180. The mass flow controller 164 is used to move the $CO_2$ gas from the reactor 119 to the detector 180. The mass flow controller 164 component allows the analyzer 100 to maintain a constant flow for sparging while being able to measure the exact pressure in the analyzer 100.

In one embodiment, the detector 180 may be an NDIR detector to measure the carbon content in the pressurized $CO_2$ gas sample when measuring IC, NPOC or TC. A pressurized detection technique (static read) enables the measurement of the specific carbon constituent contained in the sample 112. While the operating pressure is building, the carbon constituent can be oxidized and swept with an inert carrier gas such as nitrogen gas into a sealed NDIR cell detector 180 for measurement. Once all of the $CO_2$ gas has been swept from the sample 112 into the sample cell 206 of the detector 180, single or multiple measurements can be made to determine the amount of carbon constituent contained in the pressurized $CO_2$ gas contained in the detector 180. This measurement correlates directly to the concentration of the specific carbon constituent in the original sample 112 received by the analyzer 100.

One advantage of employing the pressurized technique described herein is that substantially the entire mass of the $CO_2$ gas is the particular sample being measured may be contained in the detector 180 at the same time during one or more measurements. Having substantially all of the $CO_2$ mass in the in the detector 180 at the same time may increase the sensitivity of the analysis. In various embodiments, the sensitivity may be increased up to approximately 25%. Another advantage of employing the pressurized technique is that the measurement of the concentration of $CO_2$ is made on the sample contained in the detector 180. In contrast, in conventional flow-through techniques, there is an inherent error because multiple separate measurements are made at separate times while the $CO_2$ gas sample flows through a conventional flow-through type $CO_2$ detector. These multiple measurements are then integrated to a peak. The static pressure technique described herein employed in the analyzer 100 eliminates the inherent error that is associated with the time delays between the multiple measurements. The delays add error to the integration of the $CO_2$ peak. The elimination of this inherent error in the pressurized analyzer 100 also helps to lower calculated minimum detection limits (MDL). The technique employed in the pressurized analyzer 100 also simplifies the hardware and software requirements to achieve the desired measurements for the $CO_2$ gas sample to determine the content of the carbon constituent in the sample 112.

In order to make a static measurement, the detector 180 is pressurized to an operating pressure above atmospheric pressure by the mass flow controller 164. In various embodiments, the detector 180 may be pressurized to well above atmospheric pressure such as, for example, up to 3 atmospheres above atmospheric pressure. In one embodiment, the detector 180 may be pressurized up to 2.4 atmospheres above atmospheric pressure. In terms of pounds-per-square-inch (psi), the detector 180 may be pressurized from 30 psi-60 psi above atmospheric pressure. For example, the NDIR sample cell 206 of the detector 180 may be pressurized from atmospheric pressure (e.g., about 14.7 psi) up to about three atmospheres (e.g., about 60 psi) above atmospheric pressure. In one embodiment, the detector 180 may be pressurized anywhere from atmospheric pressure up to about 30 psi above atmospheric pressure. In another embodiment, the detector 180 may be pressurized anywhere from atmospheric pressure up to about 60 psi above atmospheric pressure. In one example, the NDIR sample cell 206 may be pressurized to about 2.4 atmospheres. The mass flow controller 164 may be used to manually or automatically regulate and/or adjust the operating pressure in the detector 180 (and/or the analyzer). As previously described, the mass flow controller 164 may be used to move substantially the entire mass of $CO_2$ gas from the reactor 119 to the detector 180. The mass flow controller 164 comprises a pressure transducer to measure the operating pressure of the analyzer 100. It will be appreciated by those skilled in the art that the pressurization levels described herein are non-limiting examples. Any suitable pressure above atmosphere may be employed to pressurize the analyzer 100 (e.g., the detector 180) in accordance with the desired analysis of a particular constituent element in the sample 112. The analyzer 100 is pressurized to move substantially the entire mass of the gas sample containing the constituent of interest into the detector cell 180 for measurement purposes.

Prior to placing the analyzer 100 in an instrument condition ready to receive the sample 112, the analyzer 100 may execute a cleaning procedure to clean the sparger 115, the reactor 119 and any interconnecting lines. One technique for cleaning a liquid sample carbon analyzer is described in commonly assigned U.S. Pat. No. 6,007,777 to Purcell et al. titled "LIQUID SAMPLE CARBON ANALYZER", the entire contents of which are incorporated herein by reference. Other suitable cleaning techniques may be employed. The methods 400, 500, 600, 700 employed by the analyzer 100 to carry out the various analyses discussed below may be carried out by the computer 194 or any processor (e.g., a microprocessor-based controller) coupled to the analyzer 100.

Figure 3:
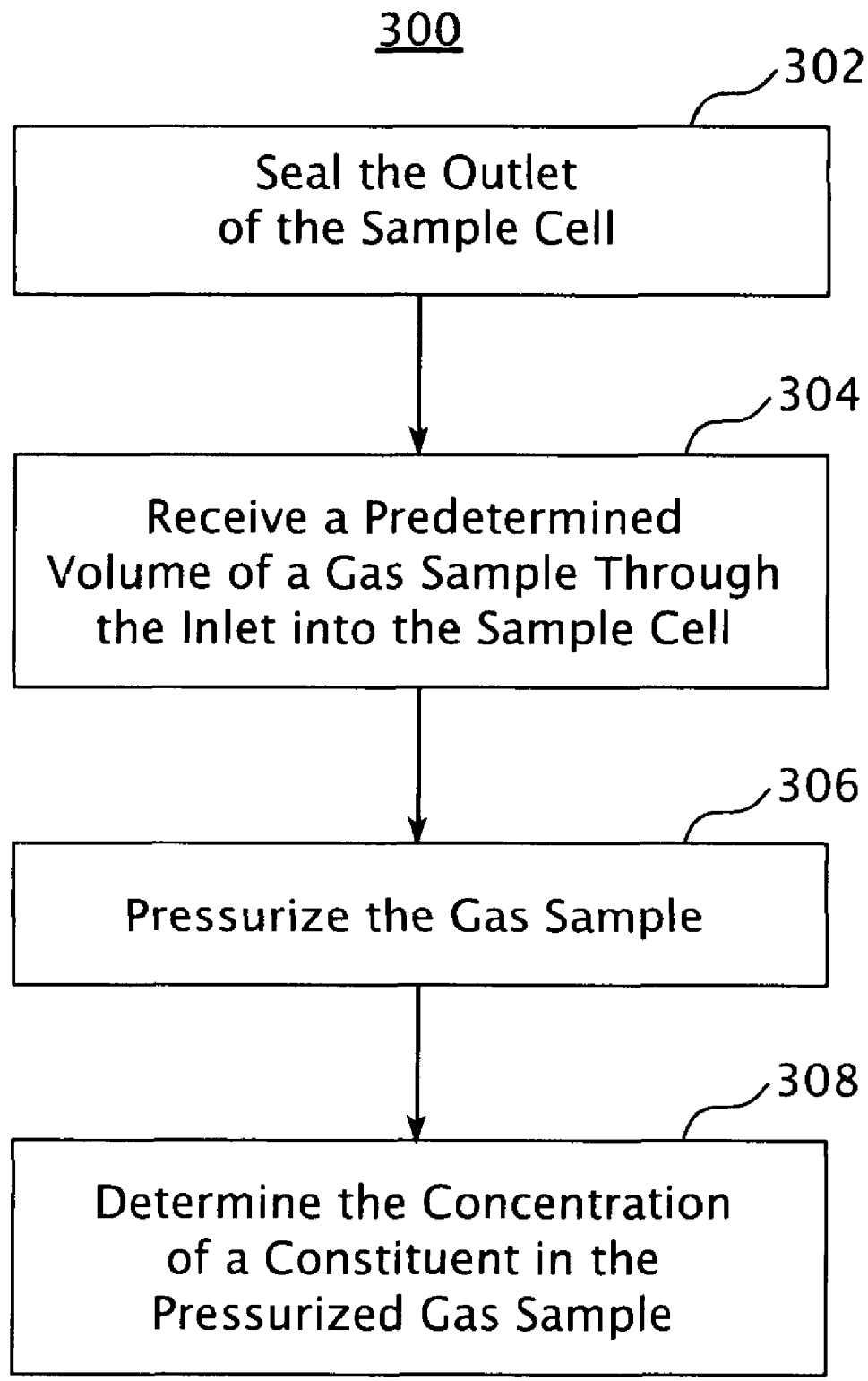
FIG. 3 illustrates one embodiment of a method for measuring the concentration of a constituent in a pressurized gas sample.

FIG. 3 illustrates one embodiment of a method 300 for measuring the concentration of a constituent element in a gas sample. In one embodiment, the outlet of the sample cell 206 of the detector 180 is sealed 302. A predetermined volume of a gas sample may be received 304 through the inlet 202 into the sample cell 206. The gas sample may be pressurized 306 above atmospheric pressure. And a concentration of a constituent in the pressurized gas sample may be determined 308.

In one embodiment, the liquid sample 112 may be received in the reactor 119 and the liquid sample 112 may be converted into the gas sample to be measured. The gas sample may be swept from the reactor 119 to the sample cell 206. A carrier gas may be received into the reactor 119 to sweep the gas sample from the reactor 119 to the sample cell 206. In the sample cell 206, the gas sample may be pressurized to a pressure above atmospheric pressure. The determining of the concentration of the constituent of the pressurized gas sample while the gas sample is in the sample cell 206 may be repeated multiple times.

In one embodiment, the liquid sample 112 may be received in the sparging chamber 114. The liquid sample 112 to be measured may be sparged with an acid 130 and the gas sample may be swept from the sparging chamber 114 to the sample cell 206. In the sample cell 206, the gas sample may be pressurized to a pressure above atmospheric pressure.

In the embodiment of the detector 200 shown in FIG. 2A, a method 300 comprises emitting a beam of incident radiation by the radiant energy source 208 along the direction indicated by arrow 209 on the pressurized gas sample contained in the sample cell 206 and determining the concentration of the constituent in the pressurized gas sample corresponding to a quantity of the radiation absorbed by the pressurized gas sample. The method 300 also may comprise interrupting the beam of incident radiation at predetermined intervals by a rotating chopper disk 214 and measuring a flow rate between a first cell and second detector cell 210, 212 using a mass flow sensor 218. The first and second detector cells 210, 212 are filled with a predetermined quantity of the constituent element to be measured in the gas sample. The flow rate may be integrated over time. The concentration of the constituent element in the pressurized gas sample may be correlated with the integrated flow rate over time.

Figure 4A:
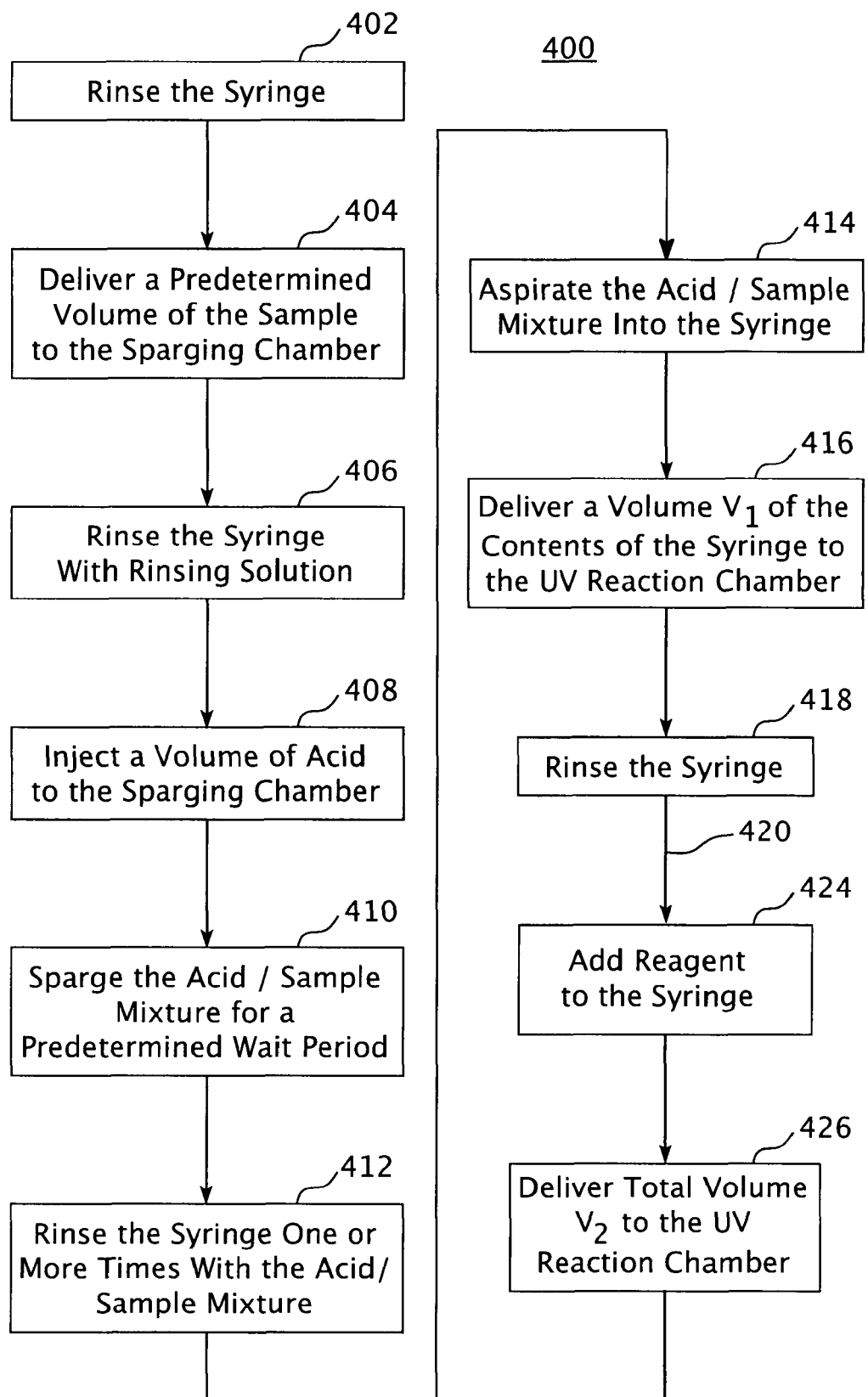
FIGS. 4A, B illustrate one embodiment of a total organic TOC/NPOC content method employed by the analyzer shown in FIG. 1 to carry out a TOC/NPOC analysis.
Figure 4B:
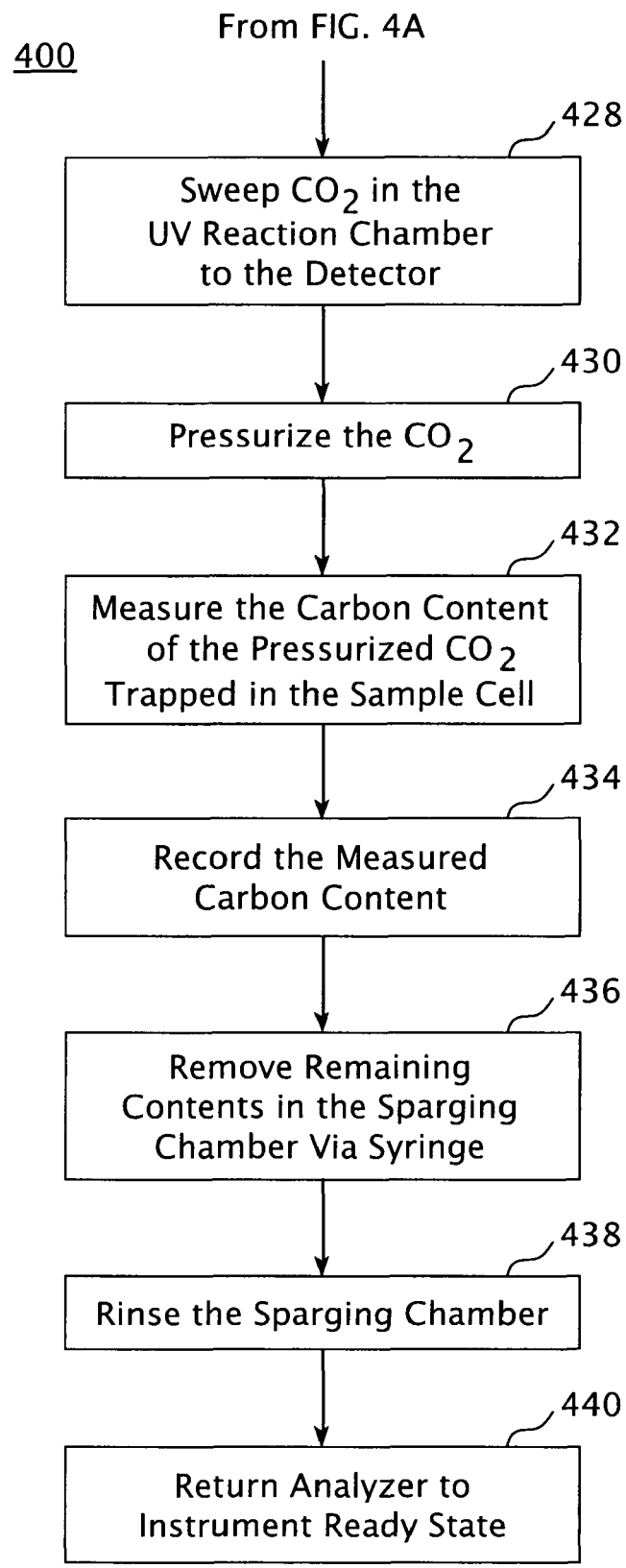

FIGS. 4A, B illustrate one embodiment of a TOC/NPOC content method 400 employed by the analyzer 100 to carry out a TOC/NPOC analysis. It is known that the TOC of many samples can be ascertained by measuring the NPOC content of such samples. First, acid 130 is added to the sample 112 and the resulting mixture is sparged in the sparger 115, thus removing the IC and POC from the sample 112. Next a persulfate solution or oxidant or other reagent 124 is added to the mixture and the resulting new mixture is exposed to UV radiation in the reactor 119. NPOC, the only remaining carbon in the sample 112, is converted to $CO_2$ gas which is pressurized above atmospheric pressure and is measured in the sample cell 206 of the detector 180 in accordance with the method 300 previously described.

The valves 154, 156, 176, 196 are "off" unless otherwise specified. After a system initialization, the syringe 102 is rinsed 402 one or more times using a predetermined volume (e.g., 1 ml) of the sample 112. The syringe 102 is loaded with the sample 112 and then discharged to waste 141. A predetermined or preprogrammed volume of the sample 112 is delivered 404 to the sparging chamber 114. The syringe 102 is rinsed 406 with water or other rinse solution 138 using the procedure previously described, and a volume of acid 130 is injected 408 through the line 116 to the sparging chamber 114. This technique permits larger volumes of the sample 112 to be delivered to the sparging chamber 114, the delivery of the acid 130 flushes any sample resident in the line 116 into the sparging chamber 114 and ensures complete processing of the programmed volume of the sample 112. In other embodiments, both the sample 112 and the acid 130 may be loaded into the syringe 102 and then delivered to the sparging chamber 114. The acid/sample mixture is sparged 410 for a predetermined or programmed period. Any $CO_2$ or any other carbon species exiting the sparging chamber 114 are released to vent through the line 170b. The syringe 102 is rinsed 412 one or more times with the acid/sample mixture being sequentially loaded and sent to waste 141. The acid/sample mixture is aspirated 414 into the syringe 102. A volume $V_1$ of the contents of the syringe 102 (acid/sample mixture) are then delivered 416 to the reaction chamber 118 where it is exposed to UV rays. The syringe 102 is rinsed 418 and control moves to a decision block. (Note: $V_2$ is defined as a previously programmed or defined volume of the reagent 124 to be mixed with the sample/acid mixture volume $V_1$.)

The desired reagent 124 volume is added 420 to the syringe 102. The reagent 124 volume $V_2$ (and the volume $V_3$ of the rinse solution, if any) is delivered 422 to the reaction chamber 118. This flushes any sample resident in the line 120 into the reaction chamber 118 to again ensure complete processing of the sample 112. In the reactor 119, the UV radiation from the lamp 122 immediately begins converting organic carbon in the sample 112 to $CO_2$ gas in the reaction chamber 118. The valves 158 and 176 are turned "on" and any $CO_2$ gas in the reaction chamber 118 is swept 428 by the carrier gas into the detector 180 sample cell 206 under system pressure as may be determined, for example, by the pressure regulator 162. As previously discussed, the analyzer 100 may be pressurized 430 from atmospheric pressure (e.g., about 14.7 psi) to about three atmospheres (e.g., about 60 psi) above atmospheric pressure. The mass flow controller 164 moves or sweeps the $CO_2$ gas from the reaction chamber 118 to the sample cell 206 of the detector 180. In the sample cell 206, the CO2 gas is maintained under system pressure before and during the measurements. The detector 180 measures 432 the carbon constituent content in the pressurized $CO_2$ gas trapped in the sample cell 206 one or multiple times in accordance with the process described in the method 300. In one embodiment, for example, the detector 180 may be implemented as a pressurized NDIR1 detector and infrared radiation may be employed to determine the carbon constituent content in the pressurized $CO_2$ gas sample trapped in the sample cell 206. The one or multiple measurements of the same pressurized $CO_2$ gas sample may be recorded 434 (e.g., stored in memory or storage or may be transmitted or otherwise communicated) by the computer 194. When the one or multiple measurements are completed, any remaining contents in the sparging chamber 114 are sent 436 to waste. The sparging chamber 114 is then rinsed 438 by transferring the now carbon-free contents of the reaction chamber 118 to the sparging chamber 114 and then expelling such contents to waste 141. The analyzer 100 then returns 440 to its instrument ready state.

It will be noted that the sparging chamber 114 may remain substantially idle after a volume $V_1$ of liquid is transferred to the reaction chamber 118. Accordingly, multiple samples 112 may be processed in a shortened overall time period. For example, while one sample is being processed in the reaction chamber 118, the sparging chamber 114 is rinsed and loaded with the next sample. IC thus may be removed from the subsequent sample in the sparging chamber 114 at the same time OC in the prior sample is being converted to $CO_2$ gas, removed from the reaction chamber 118, and detected by the detector 180. The time savings realized by this procedure may be increased where scores of samples are to be processed in sequence, such as with an autosampler.

Figure 5:
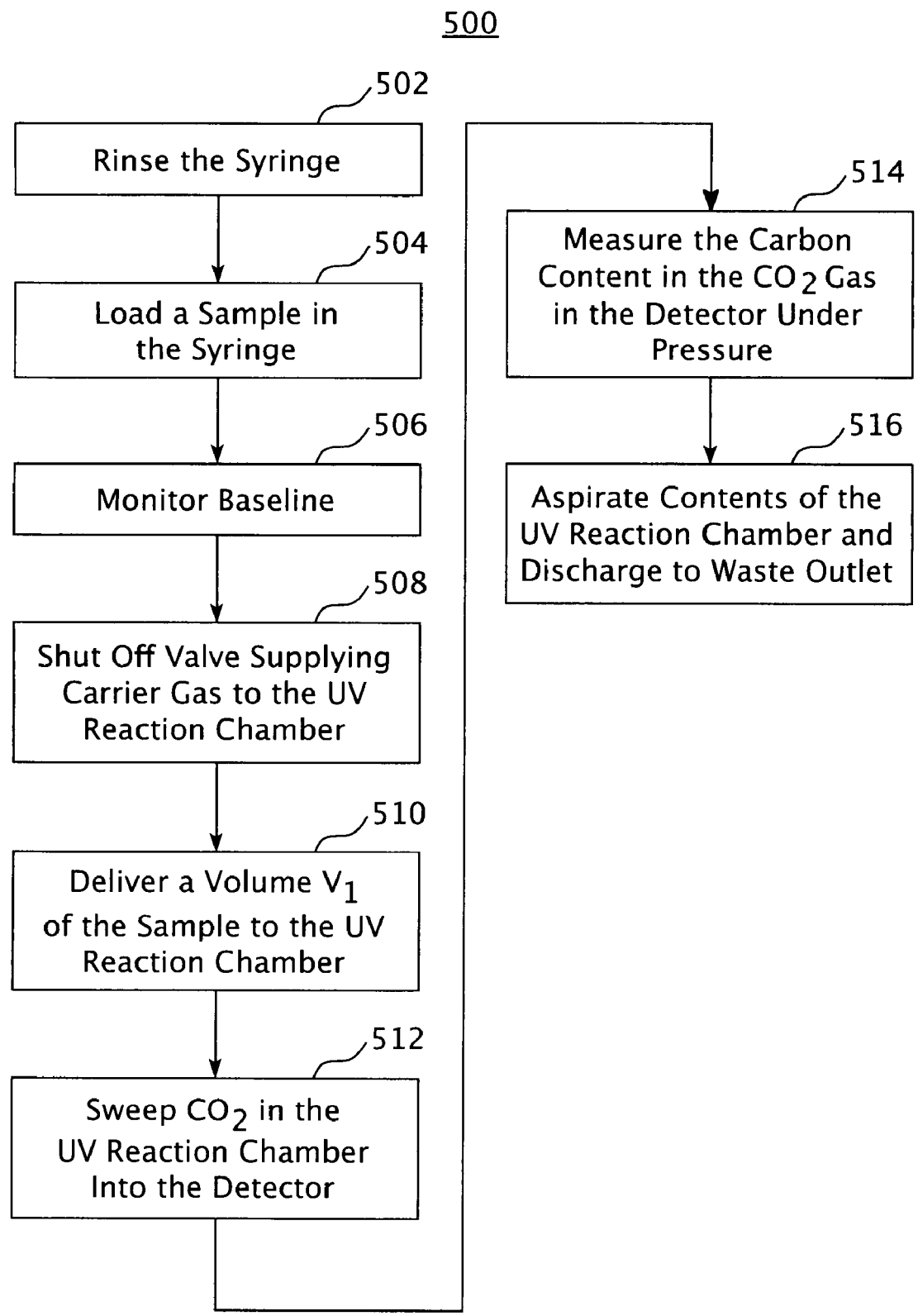
FIG. 5 illustrates one embodiment of a TC content method employed by the analyzer shown in FIG. 1 to measure the TC content of a sample.

FIG. 5 illustrates one embodiment of a TC content method 500 employed by the analyzer 100 to measure the TC content of a sample 112. In this procedure, the acid 130 and the persulfate reagent 124 may be added to the sample 112 in the reaction chamber 118, where both IC and TOC are converted to $CO_2$ gas. The $CO_2$ gas is swept out of the reaction chamber 118 by the carrier gas under system pressure and detected by the detector 180 in the pressurized sample cell 206.

At initialization, the valves 154, 156, 172, 176, 196 are set to off, on, on, on, off, respectively. This shuts off the carrier gas flow to the sparging chamber 114, turns on the carrier gas flow to the reaction chamber 118, and routes the $CO_2$ gas exiting the reaction chamber 118 to the detector 180 under the system pressure set by the pressure regulator 162. As previously discussed, the analyzer 100 may be pressurized from a pressure of about one atmosphere (e.g., about 14.7 psi) to about three atmospheres (e.g., about 60 psi) above atmospheric pressure. The syringe 102 is rinsed 502 and the sample 112 is loaded 504 into the syringe 102 thereafter. A baseline is monitored 506 and the valve 156 supplying carrier gas to the reaction chamber 118 is shut off 508 and then a volume $V_1$ of the sample 112 is delivered 510 to the reaction chamber 118. UV radiation from the lamp 122 immediately begins converting organic carbon in the sample 112 to $CO_2$ gas. The valves 158 and 176 are turned on and any $CO_2$ gas in the reaction chamber 118 is swept 512 by the carrier gas into the sample cell 206 of the detector 180 under system pressure where the carbon content in the $CO_2$ gas may be measured 514 as previously discussed. The system pressure may be set manually or automatically by the pressure regulator 162. When the measurements are completed, the reaction chamber 118 contents are aspirated to the syringe 102 pump and then discharged directly to waste 516.

Figure 6:
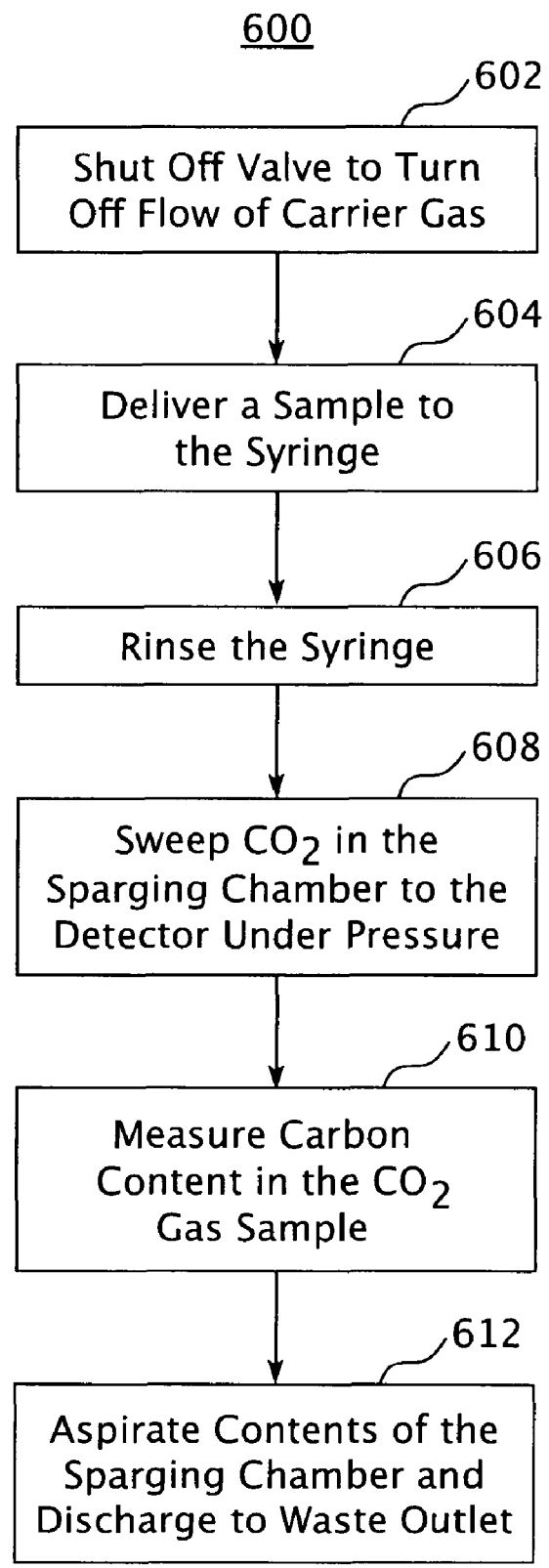
FIG. 6 illustrates one embodiment of an IC content method employed by the analyzer shown in FIG. 1 to measure the IC contents of a sample.

FIG. 6 illustrates one embodiment of an IC content method 600 employed by the analyzer 100 to measure the IC contents of the sample 112. In this procedure, the sample 112 is mixed with the acid 130 in the sparging chamber 114. IC in the sample 112 reacts with the acid 130 to form $CO_2$ gas, which is sparged out of the sample 112 and carried to the detector 180 under system pressure as previously discussed.

From the ready state the analyzer 100 is initialized. The valves 154, 156, 172, 176, 196 are set to off, on, on, on, off, respectively. The carrier gas does not flow through reaction chamber 118 but does flow through the sparging chamber 114 and from there to the $CO_2$ detector 180 under system pressure as previously discussed. The valve 154 is shut off 602, turning off the flow of the carrier gas to the sparging chamber 114 to prepare for loading the sample 112. The sample 112 is delivered 604 and the syringe 102 is rinsed 606. $V_2$ is defined as the desired acid volume. The valve 156 is turned on and the $CO_2$ gas is swept 608 to the detector 180 under system pressure as previously discussed. The contents of carbon in the $CO_2$ gas is measured 610. When the measurements are completed, a value representative of the IC is obtained by the computer 194 and stored. The sparging chamber 114 contents are aspirated to the syringe 102 pump and then discharged directly to waste 612.

Figure 7:
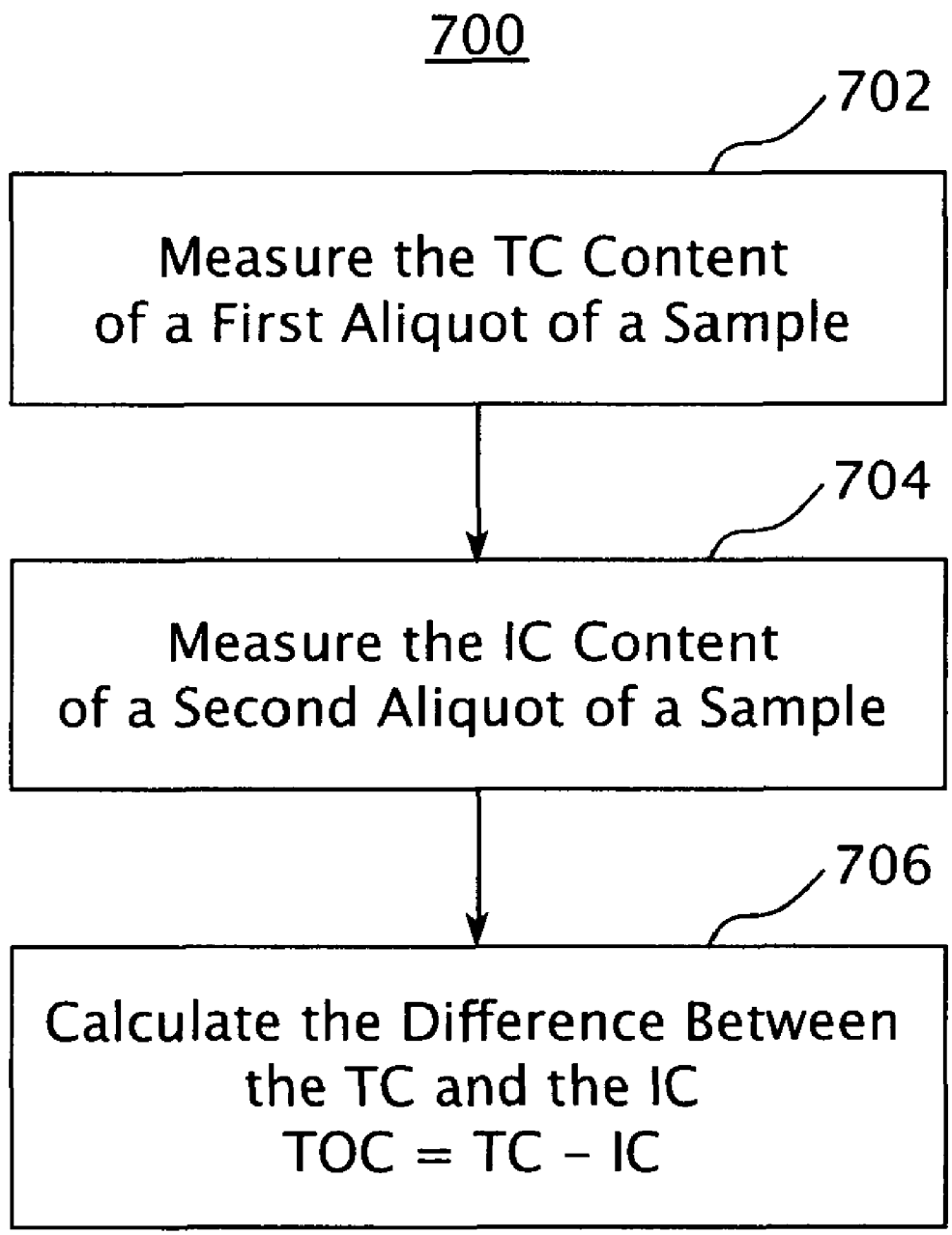
FIG. 7 illustrates one embodiment of a method employed by the analyzer shown in FIG. 1 to measure the TOC of a sample by a different procedure.

FIG. 7 illustrates one embodiment of a method 700 employed by the analyzer 100 to measure the TOC contents of a sample by a difference procedure. The amount of TOC in the sample 112 can be rigorously measured by separately measuring the sample TC and IC as discussed above. The TOC content of the sample 112 is then calculated as:

$$TOC=TC-IC.$$

Measure 702 the TC content in a first aliquot of the sample 112 according to the method 500 of FIG. 5, which first aliquot is then discharged to waste 141. Measure 704 the IC content in a second aliquot of a sample 112 according to the IC content method 600 of FIG. 6. Calculate 706 the difference between the TC and IC values to yield the TOC content of the sample 112. This may be calculated by the computer 194.

While certain features of the embodiments have been illustrated as described herein, many modifications, substitutions, changes and equivalents will now occur to those skilled in the art. It is therefore to be understood that the appended claims are intended to cover all such modifications and changes as fall within the true scope of the embodiments.

What is claimed is:

1. A method for measuring the concentration of a constituent element in a gas sample contained in an analyzer, the method comprising:
   sealing an outlet of a sample cell of a detector;
   receiving a predetermined mass of a gas sample through an inlet into the sample cell over a predetermined pressurization period during which the predetermined mass of the gas sample is received into the sample cell, wherein the entire mass of the gas sample contained in the analyzer is contained within the sample cell;
   pressurizing the gas sample contained in the sample cell to a predetermined pressure over the pressurization period; and
   determining a concentration of a constituent element in the pressurized gas sample contained in the sample cell.

2. The method of claim 1, comprising:
   emitting a beam of incident radiation on the pressurized gas sample in the sample cell.

3. The method of claim 2, comprising:
   determining the concentration of the constituent element in the pressurized gas sample in proportion to a quantity of the radiation absorbed by the pressurized gas sample.

4. The method of claim 3, comprising:
   interrupting the beam of incident radiation at predetermined intervals;
   measuring a flow rate between a first detector cell and a second detector cell, the first and second detector cells are filled with a predetermined quantity of a constituent element to be measured in the gas sample; and
   wherein the concentration of the constituent element in the pressurized gas sample is proportional to the flow rate between the first and second detector cells integrated over a predetermined period of time.

5. The method of claim 1, comprising:
   receiving a liquid sample in a reactor;
   converting the liquid sample into the gas sample to be measured; and
   sweeping the gas sample from the reactor to the sample cell during the pressurization period.

6. The method of claim 5, comprising:
   receiving a carrier gas into the reactor to sweep the gas sample from the reactor.

7. The method of claim 1, comprising:
   repeating the determining of the concentration of the constituent element of the pressurized gas sample while the pressurized gas sample is in the sample cell.

8. The method of claim 1, comprising:
   pressurizing the gas sample in the sample cell to a pressure above atmospheric pressure.

9. The method of claim 1, comprising:
   receiving a liquid sample in a sparging chamber;
   sparging the liquid sample to be measured with an acid; and
   sweeping the gas sample from the sparging chamber to the sample cell.

10. The method of claim 1, comprising:
    emitting a beam of incident radiation on the pressurized gas sample in the sample cell;
    reflecting the beam of radiation from a mirror; and
    detecting a quantity of radiation reflected from the mirror.

11. The method of claim 1, comprising determining the concentration of the constituent element in the pressurized gas sample based on the detected reflected quantity of radiation.

12. The method of claim 1, comprising:
    contacting the pressurized gas sample with a second gas sample to produce an excited state of a third gas sample; and
    detecting a quantity of light emitted within a period of time during which the excited third gas sample returns to a ground state from the excited state.

13. A method for measuring the concentration of a constituent element in a gas sample contained in an analyzer, the method comprising:
    sealing an outlet of a sample cell of a detector;
    receiving a predetermined mass of a gas sample through an inlet into the sample cell over a predetermined pressurization period during which the predetermined mass of the gas sample is received into the sample cell, wherein the entire mass of the gas sample contained in the analyzer is contained within the sample cell;
    pressurizing the gas sample contained in the sample cell to a predetermined pressure over the pressurization period;
    emitting a beam of incident radiation on the pressurized gas sample in the sample cell;
    interrupting the beam of incident radiation at predetermined intervals;
    measuring a flow rate between a first detector cell and a second detector cell, the first and second detector cells are filled with a predetermined quantity of a constituent element to be measured in the gas sample; and
    determining the concentration of the constituent element in the pressurized gas sample contained in the sample cell in proportion to a quantity of the radiation absorbed by the pressurized gas sample, wherein the concentration of the constituent element in the pressurized gas sample is proportional to the flow rate between the first and second detector cells integrated over a predetermined period of time.

14. The method of claim 13, comprising reflecting the beam of incident radiation with a mirror.

15. The method of claim 14, comprising detecting a quantity of radiation reflected from the mirror.

16. The method of claim 13, comprising:
    measuring a flow rate between a first detector cell and a second detector cell, the first and second detector cells are filled with a predetermined quantity of a constituent element to be measured in the gas sample; and
    wherein the concentration of the constituent element in the pressurized gas sample is proportional to the flow rate between the first and second detector cells integrated over a predetermined period of time.

17. A method, comprising:
    receiving a predetermined mass of a gas sample through an inlet into the sample cell over a predetermined pressurization period during which the predetermined mass of the gas sample is received into the sample cell, wherein the entire mass of the gas sample contained in the analyzer is contained within the sample cell;
    pressurizing the gas sample contained in the sample cell to a predetermined pressure over the pressurization period;
    determining a concentration of a constituent element in the pressurized gas sample contained in the sample cell; and repeating the determining of the concentration of the constituent element of the pressurized gas sample while the pressurized gas sample is in the sample cell.

18. The method of claim 17, comprising pressurizing the gas sample to 30 psi-60 psi above atmospheric pressure.

19. The method of claim 17, comprising:

emitting a beam of incident radiation on the pressurized gas sample in the sample cell;

reflecting the beam of radiation from a mirror;

detecting a quantity of radiation reflected from the mirror; and determining the concentration of the constituent element in the pressurized gas sample based on the detected reflected quantity of radiation.

20. The method of claim 19, comprising:

contacting the pressurized gas sample with a second gas sample to produce an excited state of a third gas sample; and detecting a quantity of light emitted within a period of time during which the excited third gas sample returns to a ground state from the excited state.

* * * * *